US012697357B2

(12) United States Patent
 Chin

(10) Patent No.: US 12,697,357 B2
(45) Date of Patent: Aug. 4, 2026

(54) COMPOSITION FOR TREATING BRAIN DISEASE COMPRISING *Pediococcus inopinatus* OR EXTRACELLULAR VESICLES ISOLATED THEREFROM AS ACTIVE INGREDIENT

(71) Applicant: LISCURE BIOSCIENCES CO., LTD., Seongnam-si (KR)

(72) Inventor: Hwa Sup Chin, Yongin-si (KR)

(73) Assignee: LISCURE BIOSCIENCES CO., LTD., Seongnam-si (KR)

( * ) Notice: Subject to any disclaimer, the term of this patent is extended or adjusted under 35 U.S.C. 154(b) by 627 days.

(21) Appl. No.: 18/015,783

(22) PCT Filed: Jul. 13, 2021

(86) PCT No.: PCT/KR2021/009001

§ 371 (c)(1),
(2) Date: Jan. 12, 2023

(87) PCT Pub. No.: WO2022/015033

PCT Pub. Date: Jan. 20, 2022

(65) Prior Publication Data

US 2023/0338439 A1 Oct. 26, 2023

(30) Foreign Application Priority Data

Jul. 14, 2020 (KR) ........................ 10-2020-0087033

(51) Int. Cl.
*A61K 35/744* (2015.01)
*A61P 25/28* (2006.01)

(52) U.S. Cl.
CPC ............ *A61K 35/744* (2013.01); *A61P 25/28* (2018.01)

(58) Field of Classification Search
None
See application file for complete search history.

(56) References Cited

U.S. PATENT DOCUMENTS

| | | | |
|---|---|---|---|
| 5,677,166 A | 10/1997 | Broadbent et al. | |
| 2009/0252832 A1 | 10/2009 | Falk et al. | |
| 2013/0071367 A1 | 3/2013 | Bauer et al. | |
| 2022/0016183 A1 | 1/2022 | Choi et al. | |
| 2022/0125862 A1 | 4/2022 | Choi et al. | |

FOREIGN PATENT DOCUMENTS

| | | | |
|---|---|---|---|
| CN | 108774277 A | | 11/2018 |
| EP | 3646851 A2 | | 5/2020 |
| EP | 3 912 631 A1 | | 11/2021 |
| JP | 2006-291146 A | | 10/2006 |
| KR | 20150026464 | * | 11/2015 |
| KR | 10-2016-0058229 A | | 5/2016 |
| KR | 10-161741 B1 | | 5/2016 |
| KR | 10-2017-0032845 A | | 3/2017 |
| KR | 10-2020-0088937 A | | 7/2020 |
| WO | 2020/058499 A1 | | 3/2020 |

OTHER PUBLICATIONS

Cetin et al. Biomedicine and Pharmacology. vol. 149, May 2022 pp. 1-11.*
Naz F, Siddique Y. Human Brain Disorders: A Review . Open Biol J, 2020; 8, 16 pages.*
Ojha et al Microorganisms. Apr. 20, 2023;11(4):1083, 21 pages.*
Cohen et al., "The Generation of Hydrogen Peroxide, Superoxide Radical, and Hydroxyl Radical by 6-Hydroxydopamine, Dialuric Acid, and Related Cytotoxic Agents", The Journal of Biological Chemistry, vol. 249, No. 8, Issue of Apr. 25, pp. 2447-2452, 1974 (6 pages total).
Kok Poh Loh et al., "Oxidative Stress: Apoptosis in Neuronal Injury", Current Alzheimer Research, vol. 3, pp. 327-337, 2006 (12 pages total).
Chen et al., "Role of neuroinflammation in neurodegenerative diseases (Review)", Molecular Medicine Reports, vol. 13, pp. 3391-3396, 2016 (6 pages total).
Kang et al., "Therapeutic Antiallergy Effect of Fermented Soy Curd by *Pediococcus inopinatus* Y2", Journal of Life Science, vol. 29, No. 4, pp. 478-483, 2019 (6 pages total).
Carlson, Physiology of Behavior; The 8th Edition, Chapter 2 Structure and Function of the Nervous System 077, ISBN 978-7-208-12311-3, Dec. 2014, 9 pages, with English translation.
Weidong, Cognitive Neurology, Military Medical Science Press, ISBN 978-7-5163-0003-9, Aug. 2012, 19 pages, with English translation.

* cited by examiner

*Primary Examiner* — Oluwatosin A Ogunbiyi
(74) *Attorney, Agent, or Firm* — Sughrue Mion, PLLC

(57) ABSTRACT

A composition which contains *Pediococcus inopinatus*, a culture, a lysate, an extract or a fermented product thereof, or extracellular vesicles isolated therefrom as an active ingredient, and its uses are disclosed. The composition inhibits neuroinflammation, which is a cause of a degenerative brain disease, or reduces cell death caused by oxidative stress and Amyloid β accumulation. Therefore, the composition can be utilized as an agent for preventing, ameliorating or treating various degenerative brain diseases including Alzheimer's disease and stroke. Accordingly, a method for preventing, ameliorating or treating a brain disease, by administering the composition to a subject in need thereof is disclosed.

8 Claims, 13 Drawing Sheets

200 nm

BV-2 microglial cell line

| Culture | Seeding | LB-400_CM (5%, 20%) EV LPS 5 ng/ml | Analysis |
|---------|---------|-------------------------------------|----------|

- 1 day          0 hr          10 hr          34 hr

SH-SY5Y neuroblastoma cell line

COMPOSITION FOR TREATING BRAIN DISEASE COMPRISING *Pediococcus inopinatus* OR EXTRACELLULAR VESICLES ISOLATED THEREFROM AS ACTIVE INGREDIENT

CROSS REFERENCE TO RELATED APPLICATIONS

This application is a National Stage of International Application No. PCT/KR2021/009001, filed Jul. 13, 2021, claiming priority to Korean Patent Application No. 10-2020-0087033, filed Jul. 14, 2020.

TECHNICAL FIELD

The present disclosure relates to a composition for preventing, ameliorating or treating a brain disease, which contains *Pediococcus inopinatus*, a culture, a lysate, an extract or a fermented product thereof, or extracellular vesicles isolated therefrom as an active ingredient.

BACKGROUND ART

Degenerative brain diseases refer to progressive degenerative brain diseases occurring due to selective death of neurons in specific parts of the brain because of various causes. Examples of the diseases include Alzheimer's disease, vascular dementia, Parkinson's disease, Huntington's disease, multiple sclerosis, Creutzfeldt-Jakob disease, Pick's disease and other diseases causing symptoms of dementia, such as depression, normal pressure hydrocephalus, metabolic brain disease, brain tumor, head injury, cognitive impairment and delirium.

Abnormal behaviors and disorders such as progressive cognitive dysfunction, progressive ataxia, muscle weakness, muscular atrophy, etc. occur due to causes not known thus with 1) gradual loss of the functions of specific cells in the brain and spinal cord, 2) decrease in the number of brain cells due to apoptosis, 3) death of neurons involved in the transport of neurotransmitters, 4) problem in signaling between nerves and formation or function of neural neurites and synapses and 5) reduced electrical activity of cranial nerve. In particular, Parkinson's disease is a disease wherein motor disorder, etc. occur due to the functional loss and decrease of dopamine neurons in the substantia nigra of the midbrain. Dopamine neurons are very vulnerable to oxidative stress because they form oxides through oxidative metabolism.

With the rapid global population aging, the patients with degenerative brain diseases are increasing rapidly. The Enforcement Decree of the Long-term Care Insurance Act classifies senile disease as follows according to Korean Standard Classification of Diseases: 1) Alzheimer's dementia, 2) vascular dementia, 3) dementia in other diseases classified elsewhere, 4) unspecified dementia, 5) Alzheimer's disease, 6) subarachnoid hemorrhage, 7) intracerebral hemorrhage, 8) other nontraumatic intracranial hemorrhage, 9) cerebral infarction, 10) stroke not specified as hemorrhage or infarction, 11) occlusion and stenosis of precerebral arteries, not resulting in cerebral infarction, 12) occlusion and stenosis of cerebral arteries, not resulting in cerebral infarction, 13) other cerebrovascular diseases, 14) cerebrovascular disorders in disease classified elsewhere, 15) sequelae of cerebrovascular diseases, 16) Parkinson's disease, 17) secondary parkinsonism, 18) parkinsonism in disease classified elsewhere, 19) other degenerative diseases of basal ganglia, 20) sequelae of palsy, and 21) tremor (involuntary, somewhat rhythmic, trembling of body parts).

Alzheimer's dementia is a chronic disease caused by degeneration of brain cells and gradual decline in cognitive function including memory and is characterized by gradual and fatal decline in cognitive function such as memory/judgment/language skill, etc., daily activities, personality, behavioral disorder, etc. Damage to brain cells due to excessive accumulation of amyloid beta, neurofibrillary tangles caused by hyperphosphorylation of tau protein, inflammatory response, oxidative damage, etc. is reported as its cause.

Vascular dementia refers to damage to brain tissue caused by cerebrovascular problems. Blockage or narrowing of cerebral vessels due to insufficient oxygen supply is reported as its cause.

Stroke includes ischemic stroke and hemorrhagic stroke. Ischemic stroke is caused by the partial damage of the brain caused by the blockage of cerebral vessels, and hemorrhagic stroke is caused by the rupture of cerebral vessels and pooling of blood in the affected area.

Microglia are present in the central nervous system (CNS) and are involved in the primary protection, phagocytosis and restoration of neurons. However, it is reported that activated microglia induce neuroinflammatory response. If the response persists, it can cause various neurodegenerative diseases.

It is reported that microglia activated by brain damage, brain cell death, neurotoxins, oxidative stress, etc. are involved in the pathomechanism of degenerative neurodegenerative diseases by nitric oxide (NO), reactive oxygen species (ROS), inflammatory cytokines and inflammatory enzymes. Therefore, it is expected that the amelioration of neuroinflammation through inhibition and regulation of microglial activation can play an important role in the prevention of degenerative neurodegenerative diseases. Reactive oxygen species (ROS) cause various diseases, and the overproduction/overexpression of reactive oxygen species leads to oxidative stress, cellular dysfunction and, ultimately, cell death or necrocytosis.

Under this background, prevention and treatment of degenerative brain diseases using lactic acid bacteria are being researched recently, but there is no noteworthy result yet.

The above description of the background art is provided only for enhancing the understanding the background of the present disclosure and should not be acknowledged as recognizing that it is already well known to those having ordinary knowledge in the art.

REFERENCES OF RELATED ART

Non-Patent Documents (Non-patent document 1) Cohen G, Heikkila E R. The generation of hydrogen peroxide, superoxide radical and hydroxyl radical by 6-hydrosydopamine, dialuric acid, and related cytotoxic agents. J Biol Chem. 1974; 249: 2447-52.

(Non-patent document 2) Oxidative Stress: Apoptosis in Neuronal Injury Loh K P, Huang S H, De Silva R, Tan B K, Zhu Y Z. Cuff Alzheimer Res. 3(4): 327-337. 2006.

(Non-patent document 3) Information about trend in therapeutic agents and diagnostic technologies for degenerative brain diseases such as dementia, etc., Asan Medical Center, National Institute of Food and Drug Safety Evaluation, 2019.12.

DISCLOSURE

Technical Problem

The inventors of the present disclosure have made efforts to find a lactic acid bacteria strain applicable to various kinds of brain diseases including Alzheimer's disease. As a result, they have identified that a *Pediococcus inopinatus* strain, a culture thereof or extracellular vesicles derived therefrom have the effect of inhibiting neuroinflammation, which is the cause of various brain diseases, or protecting neurons, and have completed the present disclosure.

The present disclosure is directed to providing a food composition for preventing or ameliorating a brain disease, which contains: *Pediococcus inopinatus* or a culture, a lysate, an extract or a fermented product thereof; or extracellular vesicles derived from the *Pediococcus inopinatus*, a culture or the lysate, extract or fermented product thereof; as an active ingredient.

The present disclosure is also directed to providing a pharmaceutical composition for preventing or treating a brain disease, which contains: *Pediococcus inopinatus* or a culture, a lysate, an extract or a fermented product thereof; or extracellular vesicles derived from the *Pediococcus inopinatus*, a culture or the lysate, extract or fermented product thereof; as an active ingredient.

The present disclosure is also directed to providing a method for preventing or treating a brain disease, which includes a step of administering a therapeutically effective amount of: *Pediococcus inopinatus* or a culture, a lysate, an extract or a fermented product thereof; or extracellular vesicles derived from the *Pediococcus inopinatus*, a culture or the lysate, extract or fermented product thereof; to a subject.

The present disclosure is also directed to providing a therapeutic use of a composition containing: *Pediococcus inopinatus* or a culture, a lysate, an extract or a fermented product thereof; or extracellular vesicles derived from the *Pediococcus inopinatus*, a culture or the lysate, extract or fermented product thereof The present disclosure is also directed to providing a method for preparing a composition for preventing, ameliorating or treating a brain disease, which includes a step of preparing a *Pediococcus inopinatus* strain.

The present disclosure is also directed to providing a method for preparing a composition for preventing, ameliorating or treating a brain disease, which includes a step of preparing extracellular vesicles derived from *Pediococcus inopinatus* or a culture, a lysate, an extract or a fermented product thereof.

Other purposes and advantages of the present disclosure will become more apparent by the following detailed description, claims and drawings.

Technical Solution

In an aspect, the present disclosure provides a composition for preventing, ameliorating or treating a brain disease, which contains *Pediococcus inopinatus* or a culture, a lysate, an extract or a fermented product thereof; or extracellular vesicles derived from the *Pediococcus inopinatus*, a culture or the lysate, extract or fermented product thereof; as an active ingredient.

In another aspect, the present disclosure provides a method for preventing or treating a brain disease, which includes a step of administering a therapeutically effective amount of: *Pediococcus inopinatus* or a culture, a lysate, an extract or a fermented product thereof; or extracellular vesicles derived from the *Pediococcus inopinatus*, a culture or the lysate, extract or fermented product thereof; to a subject.

In another aspect, the present disclosure provides a therapeutic use of a composition containing: *Pediococcus inopinatus* or a culture, a lysate, an extract or a fermented product thereof; or extracellular vesicles derived from the *Pediococcus inopinatus*, a culture or the lysate, extract or fermented product thereof.

The inventors of the present disclosure have made efforts to find a lactic acid bacteria strain applicable to various kinds of brain diseases including Alzheimer's disease. As a result, they have identified that a *Pediococcus inopinatus* strain, a culture thereof or extracellular vesicles derived therefrom can inhibit neuroinflammation, which is the cause of various brain diseases, reduce cell death caused by oxidative stress and Aβ (amyloid beta) accumulation or inhibit the activity of acetylcholinesterase, which is the cause of memory impairment.

In the present specification, *Pediococcus inopinatus* specifically refers to a *Pediococcus inopinatus* strain derived from kimchi. Although the *Pediococcus inopinatus* WIKIM27 strain deposited in the Korean Culture Center of Microorganisms with the accession number KCCM12653P was used as the *Pediococcus inopinatus* strain in the present disclosure, the means of acquisition is not limited thereto.

In the present specification, the *Pediococcus inopinatus* strain is a gram-positive facultative anaerobe that can grow under both aerobic and anaerobic conditions. It does not form spores, lacks motility and is sphere-shaped.

In the present specification, the *Pediococcus inopinatus* strain is a probiotic having the probiotic effect and immune-enhancing effect of general lactic acid bacteria. It is well known that the lactic acid bacteria in the genus *Pediococcus inopinatus* have probiotic effect and immune-enhancing effect.

In the present specification, the 'probiotics' are understood as live microorganisms that provide health benefits by improving the gut microbiota in animals including human. The probiotics are living microorganisms having probiotic activity and can provide beneficial effects to the gut microbiota of the host when provided to human or animals in the form of dried cells or fermented products of single or multiple strains.

In an exemplary embodiment, the present disclosure provides a composition containing *Pediococcus inopinatus* or a culture, a lysate, an extract or a fermented product thereof.

The *Pediococcus inopinatus* contained in the composition according to the present disclosure may exist as live or dead bacteria and may also exist in a dried or freeze-dried form. Lactic acid bacteria suitable for various compositions and method for preparing the same are well known to those skilled in the art. For example, the *Pediococcus inopinatus* may be a culture obtained by culturing in a known liquid or solid medium, a fermented product obtained by culturing the strain with additional ingredients, an extract obtained by extracting the strain with an organic solvent, a lysate obtained by lysing, crushing or homogenizing the cell membrane of the strain, etc., although not being limited thereto.

In a specific exemplary embodiment, the composition may be a composition containing the *Pediococcus inopinatus* strain existing as live or dead bacteria.

In another specific exemplary embodiment, the composition may be a composition containing a culture, lysate, extract or fermented product of the *Pediococcus inopinatus* strain.

In another specific exemplary embodiment, the composition may be a composition containing extracellular vesicles derived from *Pediococcus inopinatus* or a culture, a lysate, an extract or a fermented product thereof.

Extracellular vesicles (EVs) allow exchange of substances (proteins, lipids and genetic materials) between cells and function as mediators of physiological/pathological signaling. The extracellular vesicles are largely classified into exosomes and microvesicles. Exosomes have various sizes depending on their origin. They are intraluminal vesicles formed by inward budding of the endosomal membrane during maturation of multi-vesicular endosomes. They are secreted upon fusion of the multi-vesicular endosomes with the cell's plasma membrane. Microvesicles are extracellular vesicles with a size of 50-1,000 nm that are released from the plasma membrane. Individual cells produce different extracellular vesicles depending on physiological state, and secrete extracellular vesicles having specific lipid/protein/nucleic acid compositions (Jae-Wook Lee (2019). Shedding light on the cell biology of extracellular vesicles. BRIC View 2019-R03).

In the present specification, the term "extracellular vesicles" encompasses the exosomes and microvesicles.

The exosomes or extracellular vesicles have various diameters in a range of about 1-1,000 nm, specifically 10-1,000 nm, more specifically 10-800 nm, most specifically 20-600 nm.

According to an example of the present disclosure, the exosomes or extracellular vesicles derived from *Pediococcus inopinatus* according to the present disclosure had a diameter of about 10-1,000 nm (FIG. 1).

The exosomes or extracellular vesicles contained in the composition of the present disclosure are contained in large quantities in a culture (e.g., a supernatant of the culture) of *Pediococcus inopinatus*.

The exosomes or extracellular vesicles are contained in a culture (e.g., a supernatant of the culture) of *Pediococcus inopinatus* at concentrations of $1 \times 10^4$-$1 \times 10^{13}$/mL, specifically $1 \times 10^5$-$1 \times 10^{10}$/mL. The exosomes or extracellular vesicles isolated and purified therefrom may be utilized as a therapeutic agent on their own, or a culture, lysate, extract or fermented product containing a large quantity of the exosomes or extracellular vesicles may be utilized as a therapeutic agent.

In the present disclosure, the term "isolation" includes not only a process of selectively obtaining a desired substance (e.g., exosomes) from a biological sample (e.g., a *Pediococcus inopinatus* culture) (positive isolation) but also a process of selectively removing impurities other than the desired substance (negative isolation). Therefore, the term "isolation" may be used with the same meaning as "obtainment", "extraction" or "purification". In the present disclosure, the isolation of exosomes or extracellular vesicles may be performed by any method commonly employed in the art without limitation. For example, a commercially available exosome isolation kit (e.g., EXO-BB, EXOQUICK®-ULTRA, EXOQUICK®-TC, CAPTUREM™ exosome isolation kit, total exosome isolation kit, EXOTRAP™ exosome isolation spin column kit, EXO2D™, etc.) may be utilized, or separation based on the difference in the specific gravity of ingredients in a solution (e.g., centrifugation), separation based on size (e.g., ultrafiltration or vacuum filtration) or separation based on the affinity for a specific substrate (e.g., affinity chromatography) may be included. However, any separation method based on the intrinsic physical properties of a desired substance in a nonhomogeneous sample commonly used in the art may be used without limitation.

In another exemplary embodiment, the present disclosure provides a probiotic composition containing: *Pediococcus inopinatus* or a culture, a lysate, an extract or a fermented product thereof; or extracellular vesicles derived from the *Pediococcus inopinatus*, a culture or the lysate, extract or fermented product thereof.

In the present specification, the probiotic composition may be used to prevent, treat or ameliorate a gastrointestinal disease of animals including human. Specifically, the animal includes livestock such as cow, horse and pig. The 'gastrointestinal disease' includes both infection by gastroenteric harmful bacteria and inflammatory bowel disease. For example, it includes infectious diarrhea caused by pathogenic microorganisms (*E. coli, Salmonella, Clostridium*, etc.), gastrointestinal inflammation, inflammatory bowel disease, neurogenic enteritis syndrome, overproliferation of intestinal microorganisms, acute diarrhea, etc., although not being limited thereto.

Specifically, the probiotic composition according to the present disclosure is administered orally. The administration dosage may vary depending on the particular gastrointestinal disease, the severity of the disease, age, sex, race, purpose such as treatment or prevention, etc. In general, 10 million to 100 billion cells may be administered a day for an adult.

In another exemplary embodiment, the present disclosure provides a composition for enhancing immunity, which contains: *Pediococcus inopinatus* or a culture, a lysate, an extract or a fermented product thereof; or extracellular vesicles derived from *Pediococcus inopinatus* or a culture, a lysate, an extract or a fermented product thereof.

According to a specific exemplary embodiment of the present disclosure, the composition of the present disclosure is a food composition.

The *Pediococcus inopinatus* or a culture, a lysate, an extract or a fermented product thereof; or the extracellular vesicles derived from the *Pediococcus inopinatus*, a culture or the lysate, extract or fermented product thereof contained in the food composition of the present disclosure is the same as described above.

When the composition of the present disclosure is used as a food composition, the food composition may be in the form of a functional health food, a condiment, a beverage, a bar, etc. In addition, the food composition containing the strain as an active ingredient may be a beverage such as fermented milk, etc. Therefore, the present disclosure provides a lactic acid bacteria starter for fermenting food, which contains *Pediococcus inopinatus* or a culture, a lysate, an extract or a fermented product thereof; or extracellular vesicles derived from the *Pediococcus inopinatus*, a culture or the lysate, extract or fermented product thereof.

The food composition of the present disclosure may be prepared using, in addition to the active ingredient, a sitologically suitable and physiologically acceptable adjuvant. The adjuvant may be an excipient, a disintegrant, a sweetener, a binder, a coating agent, a swelling agent, a lubricant, a glidant, a flavorant, etc.

Specifically, the food composition may be prepared using one or more sitologically acceptable carrier in addition to the active ingredient described above.

For example, for preparation of a tablet or a capsule, the active ingredient may be bound with an oral, nontoxic, pharmaceutically acceptable inert carrier such as ethanol, glycerol, water, etc. In addition, if desired or necessary, a suitable binder, lubricant, disintegrant and coloring agent may also be added. Suitable binders include natural sugar such as starch, gelatin, glucose or β-lactose, corn sweetener, natural or synthetic gum such as acacia, tragacanth or sodium oleate, sodium stearate, magnesium stearate, sodium benzoate, sodium acetate, sodium chloride, etc., although not being limited thereto. The disintegrant includes starch, methyl cellulose, agar, bentonite, xanthan gum, etc., although not being limited thereto. When the composition is prepared as a liquid solution, one or more of saline, sterile water, Ringer's solution, buffered saline, albumin injection, dextrose solution, maltodextrin solution, glycerol and ethanol may be used as an acceptable pharmaceutical carrier and, if necessary, other common additives such as an antioxidant, a buffer, a bacteriostat, etc. may be used. In addition, an injectable formulation such as an aqueous solution, a suspension, an emulsion, etc., a pill, a capsule, a granule, or a tablet may be prepared by further adding a diluent, a dispersant, a surfactant, a binder or a lubricant.

The food composition according to the present disclosure may be added to various foods. The foods to which the composition of the present disclosure may be added include, for example, beverages, vitamin complexes, health supplements, etc.

The food composition of the present disclosure may contain the ingredients commonly used for preparation of food, e.g., a protein, a carbohydrate, a fat, a nutrient, a seasoning agent and a flavorant. Examples of the carbohydrate include common sugars such as monosaccharides, e.g., glucose, fructose, etc., disaccharides, e.g., maltose, sucrose, oligosaccharide, etc. and polysaccharides, e.g., dextrin, cyclodextrin, etc. and sugar alcohols such as xylitol, sorbitol, erythritol, etc. Examples of the flavorant include natural flavorants [thaumatin, *stevia* extract (e.g., rebaudioside A, glycyrrhizin, etc.)] and synthetic flavorants (saccharin, aspartame, etc.). For example, when the food composition of the present disclosure is prepared as a drink or a beverage, it may further contain citric acid, fructose syrup, sugar, glucose, acetic acid, malic acid, fruit juice, plant extracts, etc.

According to a specific exemplary embodiment of the present disclosure, the composition is a pharmaceutical composition.

In addition, the present disclosure provides a method for preventing or treating a brain disease, which includes a step of administering a therapeutically effective amount of: *Pediococcus inopinatus* or a culture, a lysate, an extract or a fermented product thereof; or extracellular vesicles derived from the *Pediococcus inopinatus*, a culture or the lysate, extract or fermented product thereof; to a subject.

In addition, the present disclosure provides a use of a composition containing: *Pediococcus inopinatus* or a culture, a lysate, an extract or a fermented product thereof; or extracellular vesicles derived from the *Pediococcus inopinatus*, a culture or the lysate, extract or fermented product thereof; for treating a brain disease.

In the present specification, the "subject" refers to a mammal which is a subject of treatment, monitoring or experiment. Specifically, it may be human or an animal in need of prevention and/or treatment of a brain disease.

According to a specific exemplary embodiment of the present disclosure, the brain disease is a degenerative brain disease.

The "degenerative brain disease" may be one or more disease selected from a group consisting of Parkinson's disease, Alzheimer's disease, Huntington's disease, Lou Gehrig's disease (amyotrophic lateral sclerosis), Creutzfeldt-Jakob disease, stroke, multiple sclerosis, learning disorder, cognitive impairment, neuroinflammation, neuronal damage and memory impairment, although not being limited thereto.

According to a specific exemplary embodiment of the present disclosure, the degenerative brain disease is Alzheimer's disease.

According to a specific exemplary embodiment of the present disclosure, the degenerative brain disease is neuroinflammation.

According to a specific exemplary embodiment of the present disclosure, the degenerative brain disease is neuronal damage.

According to a specific exemplary embodiment of the present disclosure, the degenerative brain disease is memory impairment.

According to a specific exemplary embodiment of the present disclosure, the degenerative brain disease is learning disorder.

According to a specific exemplary embodiment of the present disclosure, the degenerative brain disease is cognitive impairment.

According to a specific exemplary embodiment of the present disclosure, the composition inhibits the activity of acetylcholinesterase (AChE).

The correlation between neuroinflammation and the onset of degenerative brain diseases has been known through a number of literatures (*Mol Med Rep.* 2016 Apr. 13(4): 3391-3396; *J Immunol Res.* 2018 Apr. 16, 2018:4784268; *Transl Neurodegener.* 2015, 4: 19, etc.), and the technology of using neuroinflammatory regulators for treating degenerative brain disease is also known wells.

In addition, oxidative stress-induced cell death has been reported as the cause of various degenerative brain diseases including Alzheimer's disease and stroke (Kok Poh Loh et al., Oxidative Stress: Apoptosis in Neuronal Injury, *Curr Alzheimer Res.* 3(4): 327-337. 2006).

The composition of the present disclosure may be utilized as an agent for preventing, ameliorating or treating various degenerative brain diseases including Alzheimer's disease and stroke since it inhibits neuroinflammation, which is the cause of the degenerative brain diseases, or reduces cell death induced by oxidative stress and Aβ (amyloid beta) accumulation.

In the present specification, the "memory impairment" or "cognitive impairment" refers to memory decline, memory disorder or cognitive decline occurring as the brain shrinks and brain cells are destroyed due to physical fatigue, insufficient sleep, excessive alcohol intake, dementia and other brain diseases. The prevention, amelioration or treatment of "memory impairment" or "cognitive impairment" refers to the effect of maintaining cognitive ability by regulating harmful substances that damage brain cells or improving declined cognitive ability by regulating neurotransmitters of the brain. The memory refers to the ability of storing information in the brain and retrieving it when necessary, and the cognitive ability refers to the ability of differentiating and recognizing things.

The pharmaceutical composition according to the present disclosure may be administered orally or parenterally.

The parenteral administration can be achieved, for example, by intravenous injection, transdermal administration, subcutaneous injection, intramuscular injection, intravitreal injection, eye drop administration, intracerebroventricular injection, intrathecal injection, intraamniotic injection, intraarterial injection, intraarticular injection, intracardiac injection, intracavernous injection, intracerebral injection, intracisternal injection, intracoronary injection, intracranial injection, intradural injection, epidural injection, intrahippocampal injection, intranasal injection, intraosseous injection, intraperitoneal injection, intrapleural injection, intraspinal injection, intrathoracic injection, intrathymic injection, intrauterine injection, intravaginal injection, intraventricular injection, intravesical injection, subconjunctival injection, intratumoral injection, topical injection, etc.

The pharmaceutical composition of the present disclosure may contain a pharmaceutically acceptable carrier. In the present disclosure, the term "pharmaceutically acceptable carrier" refers to a carrier or diluent which does not cause significant irritation to an organism and does not abrogate the biological activity and properties of the administered ingredient. In the present disclosure, the pharmaceutically acceptable carrier may be one or more of saline, sterile water, Ringer's solution, buffered saline, dextrose solution, maltodextrin solution, glycerol and ethanol. If necessary, an injectable formulation suitable for injection to tissues or organs may be prepared by adding commonly used other additives such as an antioxidant, a buffer, a bacteriostat, etc. In addition, it can be formulated into a dried preparation (particularly, a freeze-dried preparation) that can be prepared into an injectable solution by adding an isotonic sterile solution or, in some cases, sterile water or physiological saline. In addition, a target organ-specific antibody or ligand can be bound to the carrier so as to allow specific action on the target organ. Suitable preparations well known in the art are disclosed in Remington's Pharmaceutical Science (Mack Publishing Company, Easton PA).

Specifically, the composition of the present disclosure may further contain a filler, an excipient, a disintegrant, a binder, a glidant, etc. In addition, the composition of the present disclosure may be formulated by a method well known in the art so as to provide quick, sustained or delayed release of the active ingredient after administration to a mammal.

In the present disclosure, the "administration" refers introduction of the composition of the present disclosure to a patient by any suitable means. The composition of the present disclosure may be administered through various oral or parenteral routes as long as it can reach the target tissue.

For example, the composition of the present disclosure may be administered clinically by intramuscular, intravenous or intraperitoneal injection.

For injection, it may be specifically formulated into a pharmaceutically suitable buffer such as Hank solution, Ringer solution or physiological saline buffer. For transmucosal administration, a penetrant suitable for the corresponding barrier is used. Such penetrants are generally known in the art.

Formulations for parenteral administration include a sterilized aqueous solution, a nonaqueous solution, a suspension, an emulsion, etc. For the nonaqueous solution or suspension, propylene glycol, polyethylene glycol, vegetable oil such as olive oil, an injectable ester such as ethyl oleate, etc. may be used.

In the present specification, the "effective amount" or "therapeutically effective amount" refers to an amount necessary to delay or completely stop the onset or progress of a specific disease desired to be treated, and the effective amount of *Pediococcus inopinatus* contained in the food composition or pharmaceutical composition of the present disclosure means the amount required to achieve the effect of preventing, ameliorating or treating a brain disease. Accordingly, the effective amount may be controlled depending on various factors including the kind of the disease, the severity of the disease, the kinds and contents of other ingredients contained in the composition, the age, body weight, general health condition and diet of a patient, administration time, administration route, treatment period, and co-administered drugs. It is obvious to those skilled in the art that an appropriate daily administration dosage can be determined adequately by a physician.

For the purpose of the present disclosure, it is desired that the therapeutically effective amount for a particular patient is varied depending on various factors such as the response desired to be achieved, the particular composition, the age, body weight, general health condition, sex and diet of a patient, administration time, administration route, the excretion rate of the composition, treatment period, and co-administered drugs, and other similar factors well known in the medical field.

In the present specification, the "treatment" refers to an approach to achieve a favorable or desired clinical result. For the purpose of the present disclosure, the favorable or desired clinical result includes nonrestrictively the amelioration of symptoms, the reduction in the reduction of the scope of diseases, the stabilization (i.e., prevention of aggravation) of disease state, the delay or slowing of disease progress, and the amelioration or temporary alleviation and reduction of disease state (partially or completely). In addition, the "treatment" may also mean increasing survival rate as compared to that expected when the treatment is not given. The "treatment" includes both therapeutic treatment and preventive measure. The treatment includes the treatment of not only a disorder to be prevented but also a disorder that has occurred already. The "alleviation" of a disease refers to the reduction of the scope of disease state and/or undesired clinical symptoms and/or the delay or extension of the time course of progress as compared to the absence of the treatment.

In another exemplary embodiment, the present disclosure provides a feed additive or a feed containing: *Pediococcus inopinatus* or a culture, a lysate, an extract or a fermented product thereof; or extracellular vesicles derived from the *Pediococcus inopinatus*, a culture or the lysate, extract or fermented product thereof; as an active ingredient.

When used as a feed additive, the composition may be prepared in the form of a 20-90% concentrate, powder or granule. The feed additive may further contain one or more of an organic acid such as citric acid, fumaric acid, adipic acid, lactic acid, malic acid, etc., a phosphate such as sodium phosphate, potassium phosphate, acid pyrophosphate, polyphosphate, etc., and a natural antioxidant such as polyphenol, catechin, α-tocopherol, rosemary extract, vitamin C, green tea extract, licorice extract, chitosan, tannic acid, phytic acid, etc. When used as a feed, the composition may be formulated into a common feed form and may contain common feed ingredients.

The feed additive and feed may further contain a dried ingredient selected from a grain, e.g., ground or crushed wheat, oats, barley, corn or rice, a vegetable protein feed, e.g., a feed having rape, bean and sunflower as main ingredients, an animal protein feed, e.g., blood meal, meat meal, bone meal or fish meal, a sugar, a dairy product, e.g., powdered milk or whey powder, etc., and may further contain a nutritional supplement, a digestion- and absorption-improving agent, a growth-promoting agent, etc.

The feed additive may be administered to an animal either alone or in combination with another feed additive in an edible carrier. In addition, the feed additive may be easily administered to an animal by directly mixing with an animal feed as a top dressing or as an oral formulation separately from the feed. When the feed additive is administered separately from the animal feed, it may be prepared as an immediate or sustained release formulation in combination with a sitologically acceptable edible carrier, as well known in the art. The edible carrier may be solid or liquid, for example, cornstarch, lactose, sucrose, bean flake, peanut oil, olive oil, sesame oil and propylene glycol. When a solid carrier is used, the feed additive may be a tablet, a capsule, a powder, a troche, a sugar-coated tablet or a non-dispersed top dressing. When used as a liquid carrier, the feed additive may be a soft gelatin capsule, a syrup, a suspension, an emulsion or a solution.

In addition, the feed additive and the feed may contain an adjuvant, e.g., a preservative, a stabilizer, a wetting agent, an emulsifier, a solubilizer, etc. The feed additive may be used by adding to an animal feed by spraying or mixing.

The feed or feed additive of the present disclosure may be applied to animal feeds for mammals, poultry and fish. It may be used for mammals such as pig, cow, sheep, goat, experimental rodents, pets (e.g., dog or cat), etc., poultry such as chicken, turkey, duck, goose, pheasant, quail, etc., and fish such as trout, etc., although not being limited thereto.

The feed or feed additive of the present disclosure may be used in animal feeds for enhancing the growth, immunity, etc. of animals.

The amount of the *Pediococcus inopinatus* strain contained in the composition according to the present disclosure may be about $10^6$-$10^{12}$ cfu/mL, e.g., $10^7$-$10^{11}$ cfu/mL or $10^6$-$10^{10}$ cfu/mL, for a single administration. Specifically, the strain may be administered in the form of live bacteria, and may be killed or attenuated before administration. In addition, when the composition is prepared using a supernatant of a culture, it may pass through an additional sterilization process by heating. The amount of the strain necessary to provide minimum effect may vary depending on the physical or health condition of a subject. In general, a daily administration dosage may be about $10^6$-$10^{12}$ cfu/mL, e.g., $10^7$-$10^{11}$ cfu/mL or $10^8$-$10^{10}$ cfu/m L.

In another exemplary embodiment, the present disclosure provides a method for preparing a composition for preventing, ameliorating or treating a brain disease, which includes:

(a) a step of preparing a *Pediococcus inopinatus* strain; and (b) a step of culturing the strain in a culture medium.

According to a specific exemplary embodiment of the present disclosure, the preparation method further includes a step of separating extracellular vesicles from the strain or the culture medium.

In another exemplary embodiment, the present disclosure provides a method for preparing a composition for preventing, ameliorating or treating a brain disease, which includes a step of preparing extracellular vesicles derived from the *Pediococcus inopinatus* strain.

The advantages and features of the present disclosure and the methods for achieving the same will become more apparent by the examples described below. However, the present disclosure is not limited by the examples but may be embodied in various different forms. The examples are provided so that the disclosure of the present disclosure is complete and the scope of the present disclosure can be clearly understood by those having ordinary knowledge in the art to which the present disclosure belongs, and the scope of the present disclosure is defined only by the appended claims.

Advantageous Effects

The features and advantages of the present disclosure may be summarized as follows:

(i) The present disclosure provides a composition for preventing, ameliorating or treating a brain disease, which contains: *Pediococcus inopinatus* or a culture, a lysate, an extract or a fermented product thereof; or extracellular vesicles derived from the *Pediococcus inopinatus*, a culture or the lysate, extract or fermented product thereof; as an active ingredient.

(ii) The composition of the present disclosure inhibits neuroinflammation, which is a cause of a degenerative brain disease, or reduces cell death caused by oxidative stress and Aβ accumulation. Therefore, it can be utilized as an agent for preventing, ameliorating or treating various degenerative brain diseases including Alzheimer's disease and stroke.

BEST MODE

Hereinafter, the present disclosure is described in more detail through examples. These examples are provided only to specifically describe the present disclosure, and it will be obvious to those having ordinary knowledge in the art that the scope of the present disclosure is not limited by the examples.

EXAMPLES

1. Preparation of Strain

A *Pediococcus inopinatus* LB-400 strain (accession number KCCM12653P, Korean Culture Center of Microorganisms) was inoculated to an MRS broth medium to 1% and cultured for 24 hours. Then, after conducting centrifugation at 3500 rpm for 10 minutes at 4° C., the remaining MRS broth medium was removed by washing the bacteria with PBS (phosphate-buffered saline). Subsequently, the bacteria homogenized in PBS were prepared at 10-fold (MOI=10), 1-fold (MOI=1) and 0.1-fold (MOI=0.1) for treatment to cells.

2. Preparation of Culture of Strain

A *Pediococcus inopinatus* LB-400 strain was inoculated to an MRS broth medium to 1% and cultured for 24 hours. Then, after conducting centrifugation at 3500 rpm for 10 minutes at 4° C., the remaining MRS broth medium was removed by washing the bacteria with PBS (phosphate-buffered saline). Subsequently, the bacteria were inoculated to a DMEM (Dulbecco's modified Eagle's medium, Welgene, Korea) at $1 \times 10^9$ CFU/mL and cultured at 30° C. for 24 hours. Then, a culture obtained by centrifuging the same at 8,000 rpm for 5 minutes at 4° C. was adjusted to pH 7.2 and then filtered with a syringe filter (pore size=0.2 μm).

3. Isolation of Extracellular Vesicles (EVs) from Culture of Strain

After fractionating the culture of the *Pediococcus inopinatus* LB-400 strain to 100 kDa and 300 kDa using a centrifugal filter, samples were obtained by finally treating with a 0.22 μm filter. As a result of comparing the content of extracellular vesicles in the fractions using Nanosight LM 10 (Malvern Panalytical, Korea), the contents of the particles with cuff of values of 0-100, 100-300 and 300 or higher were 35%, 35% and 30%, respectively ($4 \times 10^7$ particles/m L).

4. SEM Imaging of Extracellular Vesicles

Figure 1:
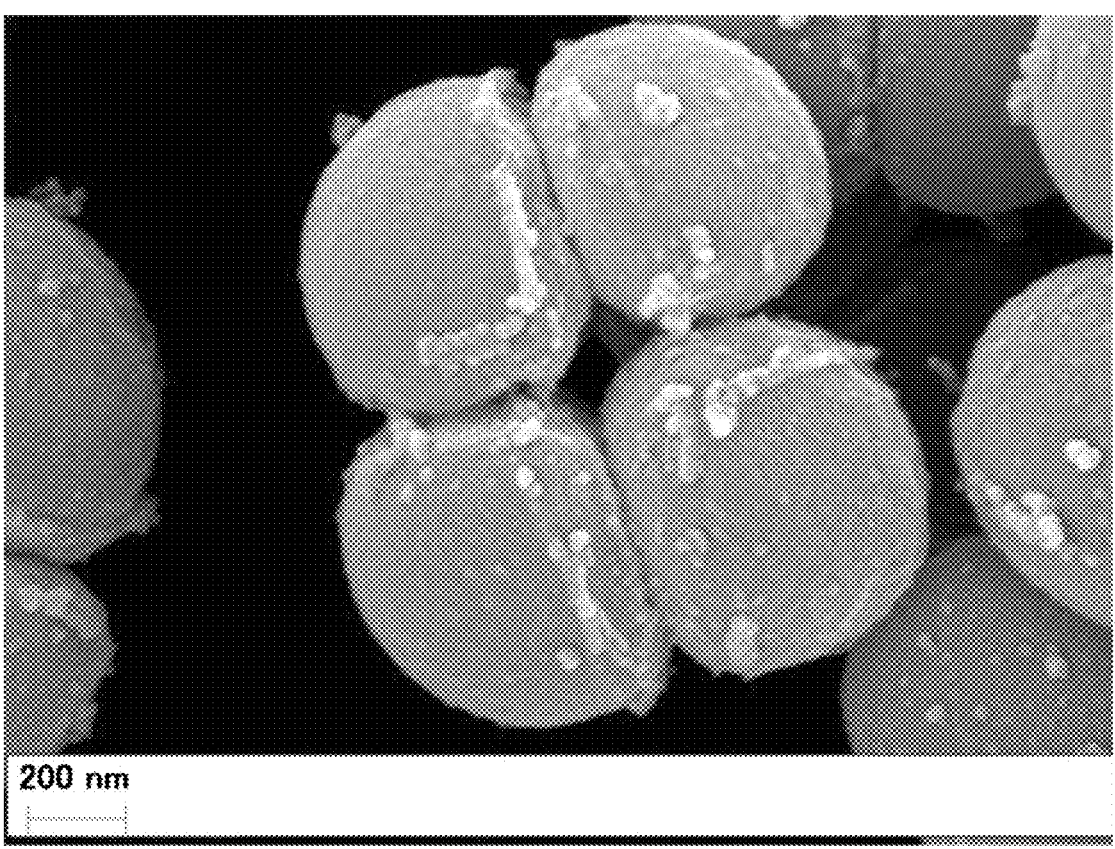
FIG. 1 shows an SEM (scanning electron microscopy) image showing the surface structure of a *Pediococcus inopinatus* LB-400 strain from the supernatant of a culture obtained by culturing the strain for 24 hours.

After washing the prepared *Pediococcus inopinatus* LB-400 strain twice with 0.1 M PB (phosphate buffer) for 30 minutes, followed by post-fixation in $OsO_4$ for 2 hours, the strain was dehydrated sequentially with 50-100% ethanol. Then, after sufficiently drying using a critical point dryer (Leica EM CPD 300), followed by platinum coating using an ion sputter (Leica EM ACE600), the strain was imaged by field emission scanning electron microscopy (FE-SEM Merlin, Zeiss) (FIG. 1).

5. Preparation of Microglia

Figure 2:
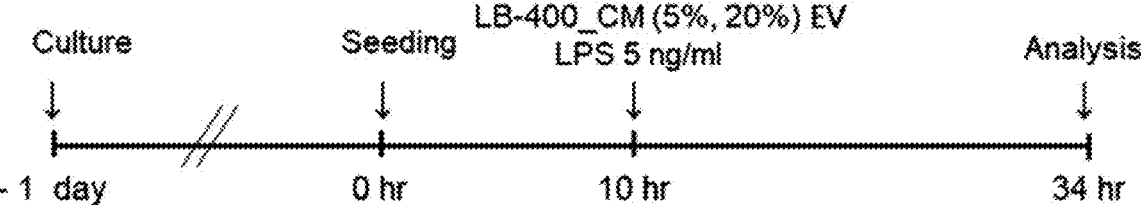
FIG. 2 schematically illustrates an experimental procedure of identifying the anti-inflammatory effect of a culture of a *Pediococcus inopinatus* LB-400 strain in BV-2 cells, which are microglial cells involved in neuroinflammation in the brain.

For testing of anti-neuroinflammatory response, microglia (BV-2 cells) acquired from Ewha Womans University were cultured in DMEM containing 5% FBS (fetal bovine serum) (GIBCO, BRL) and 1% penicillin/streptomycin (Welgene, Korea) in a 5% $CO_2$ incubator at 37° C. (FIG. 2).

6. Preparation of Neuroblastoma

Figure 3:
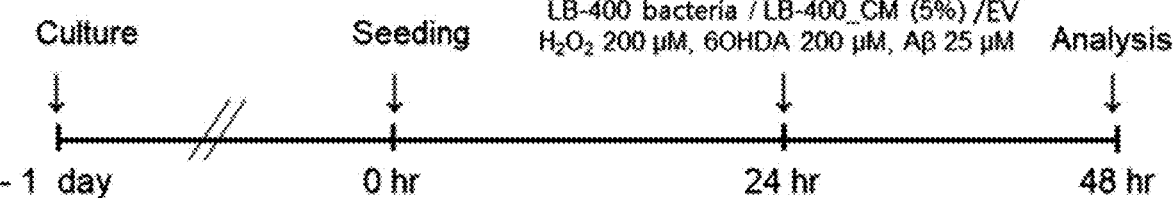
FIG. 3 schematically illustrates an experimental procedure of identifying the neuron-protecting effect of a *Pediococcus inopinatus* LB-400 strain and a culture thereof in SH-SY5Y cells, which are neuroblastoma cells involved in neuronal death in the brain.

For testing of neuron-protecting effect, neuroblastoma (SH-SY5Y cells, Cat. 22266, Korean Cell Line Bank) were cultured in DMEM/F-12 containing 10% FBS (fetal bovine serum) (GIBCO, BRL) and 1% penicillin/streptomycin (Welgene, Korea) in a 5% $CO_2$ incubator at 37° C. (FIG. 3).

Figure 4A:
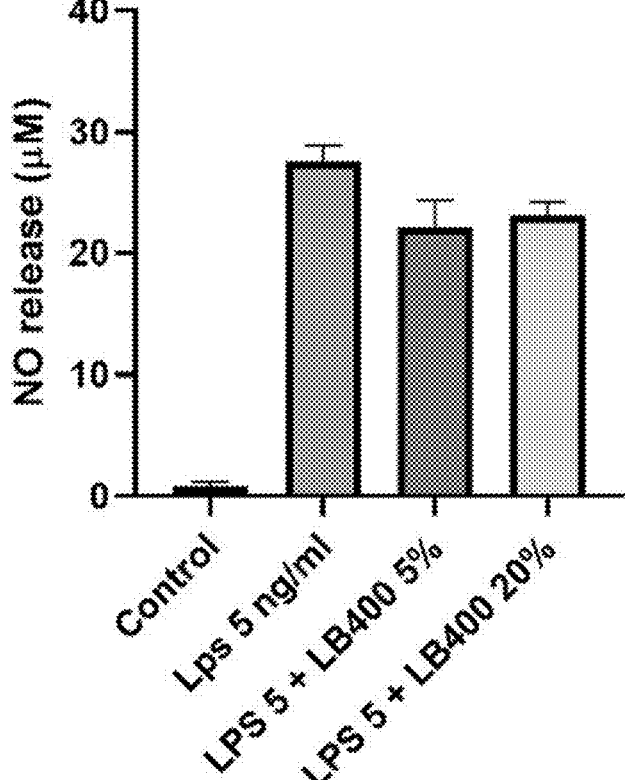
FIGS. 4A and 4B show a result of measuring the inflammatory marker NO (nitric oxide) released when microglia in which inflammation is induced by LPS are treated with a culture of a *Pediococcus inopinatus* LB-400 strain of the present disclosure (FIG. 4A) or extracellular vesicles (EVs) derived from the LB-400 strain (FIG. 4B) by Griess assay at 540 nm.
Figure 4B:
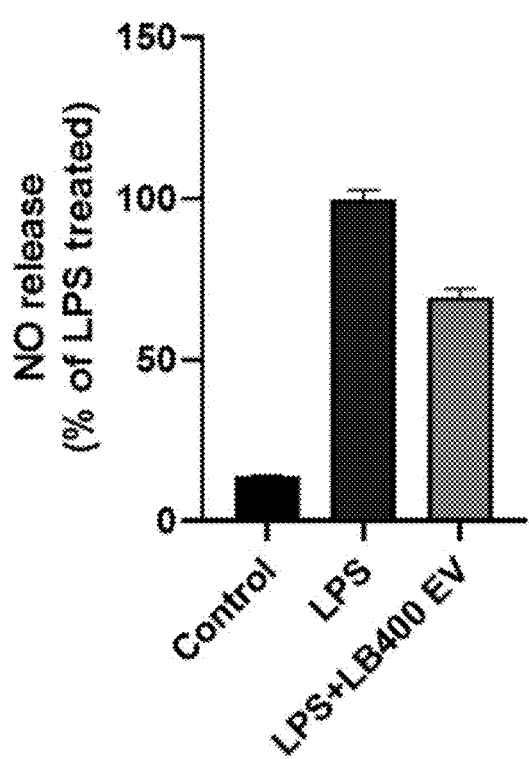

7. Investigation of Neuroinflammation-Inhibiting Effect of Culture of *Pediococcus inopinatus* and EVs In order to investigate the neuroinflammation-inhibiting effect of the culture of a *Pediococcus inopinatus* LB-400 strain (FIG. 4a) and extracellular vesicles (EVs) derived from the LB-400 strain (FIG. 4b), BV-2 microglial cells were treated at $2 \times 10^5$ cell/mL. The culture of LB-400 was diluted with a medium to 5% or 20%. LPS (lipopolysaccharide) was diluted with a medium to 5 ng/mL (FIG. 4). EVs were treated at $1 \times 10^7$ particles/mL, and a control group (con) was treated with PBS of the same volume.

Figure 6:
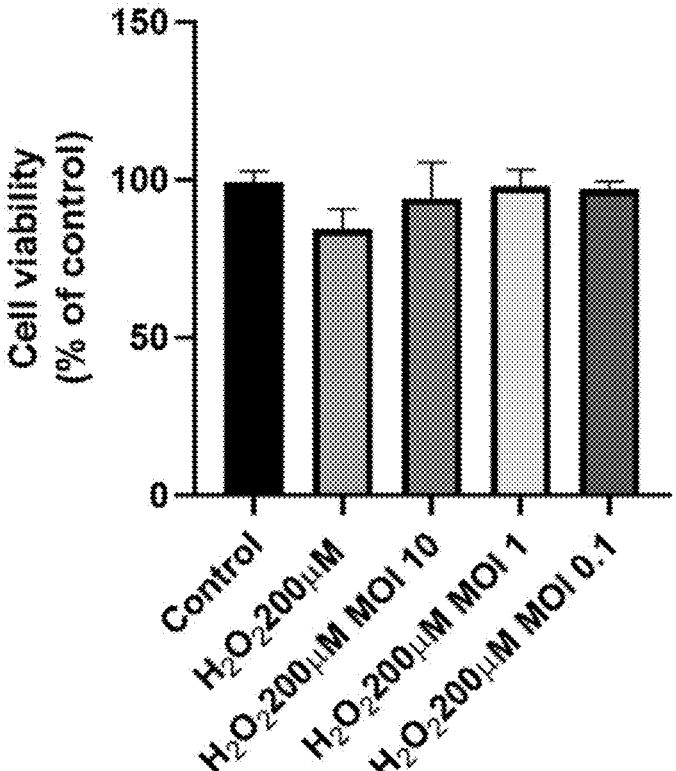
FIG. 6 shows a result of investigating the protection of nerves from oxidative stress in neuroblastoma in which oxidative stress-induced cell death is induced by $H_2O_2$ (hydrogen peroxide) by a *Pediococcus inopinatus* LB-400 strain of the present disclosure by WST assay at 450 nm.
Figure 7A:
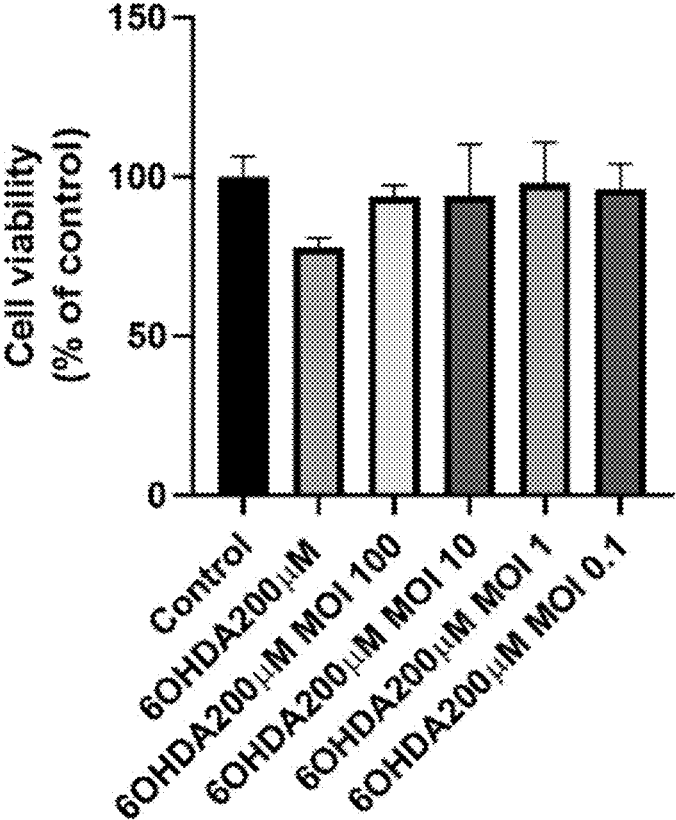
FIGS. 7A-7C show a result of investigating the protection of nerves from oxidative stress in neuroblastoma in which oxidative stress-induced cell death is induced by 6-OHDA (6-hydroxydopamine) by a *Pediococcus inopinatus* LB-400 strain of the present disclosure (FIG. 7A) and extracellular vesicles (EVs) derived from the LB-400 strain (FIGS. 7B and 7C) by WST assay (FIG. 7a), trypan blue exclusion assay (FIG. 7B) and cell images (FIG. 7C).

8. Investigation of Neuron-Protecting Effect of *Pediococcus inopinatus* and EVs In order to investigate the neuron-protecting effect of the *Pediococcus inopinatus* LB-400 strain, the LB-400 bacteria were treated with SH-SY5Y neuroblastoma cells at $1 \times 10^6$ cell/mL, at 10-fold (MOI=10), 1-fold (MOI=1) and 0.1-fold (MOI=0.1). EVs were treated at $4 \times 10^6$ particle/mL. $H_2O_2$ (hydrogen peroxide) (FIG. 6) and 6-OHDA (6-hydroxydopamine) (FIG. 7) were used after diluting in a medium to 200 μM. A control group (con) was treated with PBS of the same volume.

9. Investigation of Neuron-Protecting Effect of Culture of *Pediococcus inopinatus*

Figure 8:
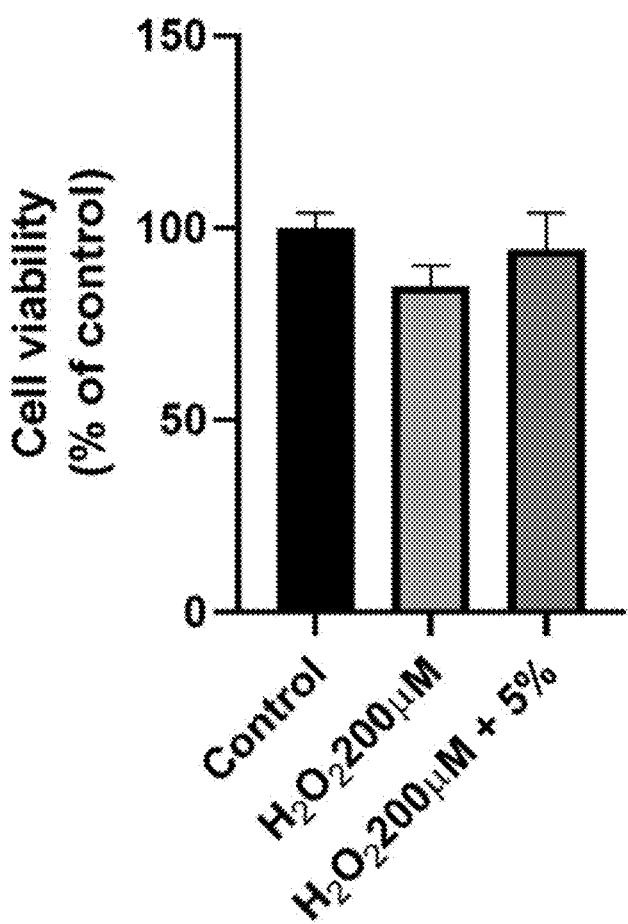
FIG. 8 shows a result of investigating the protection of nerves from oxidative stress in neuroblastoma in which oxidative stress-induced cell death is induced by $H_2O_2$ (hydrogen peroxide) by a *Pediococcus inopinatus* LB-400 strain of the present disclosure by WST assay at 450 nm.
Figure 9:
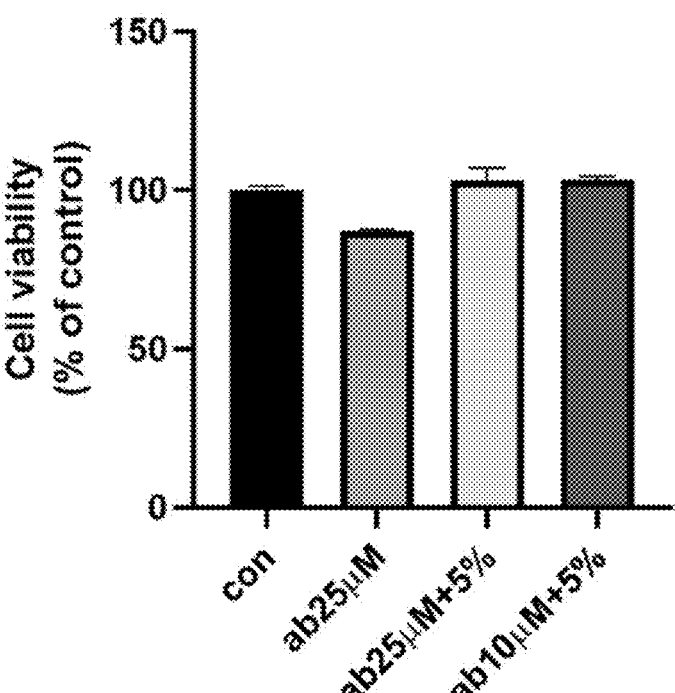
FIG. 9 shows a result of investigating the protection of nerves in which cell death is induced by Aβ (amyloid beta) accumulation by a culture of a *Pediococcus inopinatus* LB-400 strain of the present disclosure by WST assay at 450 nm.

In order to investigate the neuron-protecting effect of the *Pediococcus inopinatus* LB-400 strain, SH-SY5Y neuroblastoma cells were treated at $1 \times 10^6$ cell/m L. The culture of LB-400 was diluted with a medium to 5%. $H_2O_2$ (Hydrogen peroxide) (FIG. 8) was used after diluting in a medium to 200 μM, and Aβ (amyloid beta) (FIG. 9) used after diluting in a medium to 25 μM.

10. NO Assay

After reacting 100 μL of a supernatant with 100 μL of a Griess reagent (1% sulfanilamide, 0.1% N-(1-naphthyl)-ethylenediamine dihydrochloride, 2.5% $H_3PO_4$), nitric oxide production was measured at 540 nm using a Multiskan sky 96-well microplate spectrophotometer (Thermo Scientific, USA) (FIG. 4).

11. WST-8 Cell Viability Assay

Figure 5:
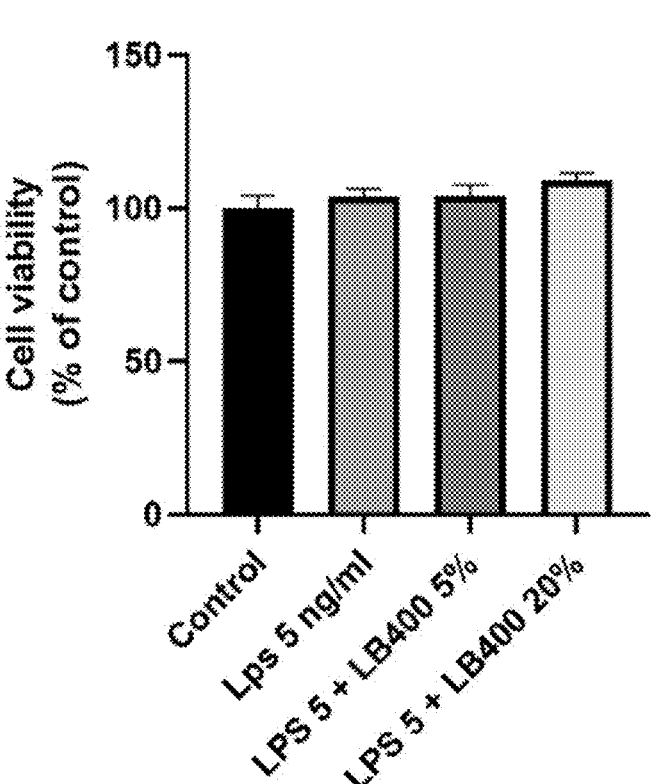
FIG. 5 shows a result of investigating the cytotoxicity of a culture of a *Pediococcus inopinatus* LB-400 strain of the present disclosure in microglia in which inflammation is induced by LPS by WST-8 assay at 450 nm.

WST-8 assay is a colorimetric method for quantification of living cells. After treating cells with 10 μL of Quanti-Max WST-8 per well and incubating in a $CO_2$ incubator for 1 hour, cell viability was measured at 450 nm using a Multi-skan sky 96-well microplate spectrophotometer (Thermo Scientific, USA) (FIG. 5).

12. Trypan Blue Exclusion Assay

Figure 7B:
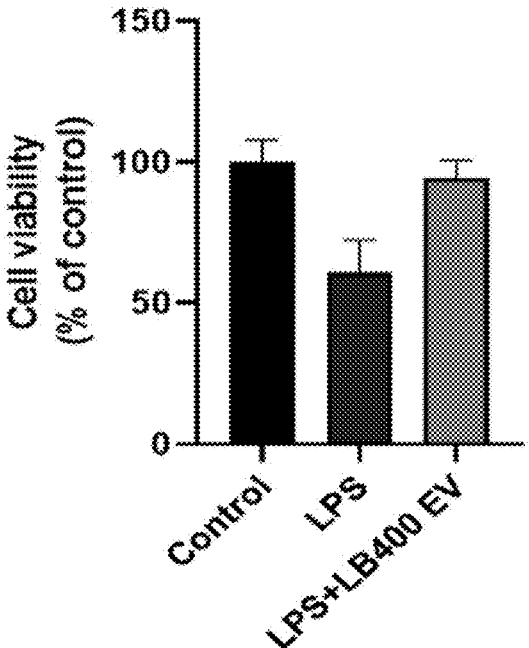
Figure 7C:
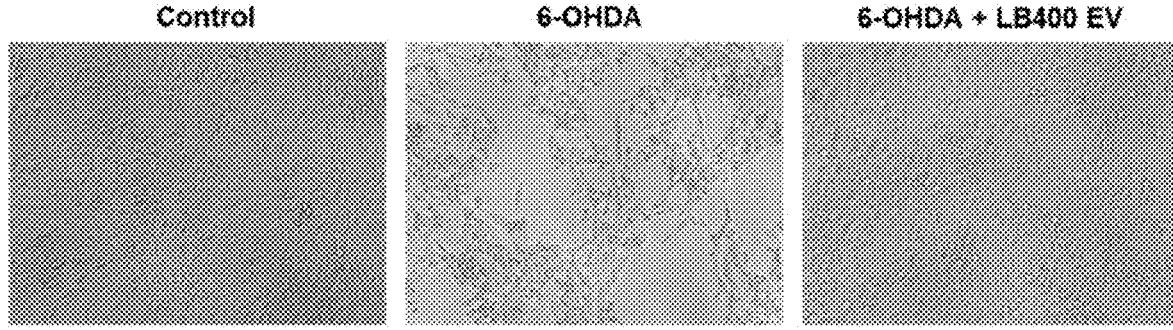

Living cells were stained with trypan blue. After treating cells with extracellular vesicles (EVs) derived from the *Pediococcus inopinatus* LB-400 strain and 6-OHDA, the cell suspension was mixed with trypan blue at 1:1. After conducting reaction for 2 minutes, the number of cells was counted under a phase-contrast microscope. Cell viability was determined by calculating the percentage of unstained cells (FIG. 7b).

Figure 10A:
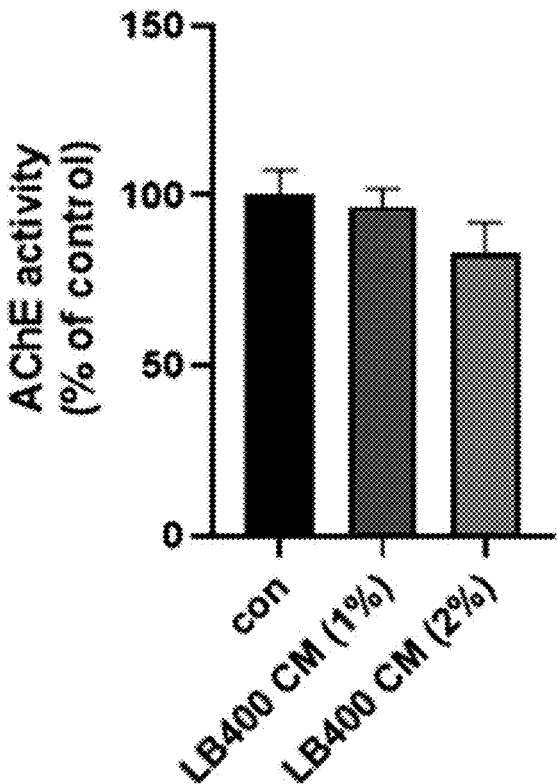
FIGS. 10a and 10b show a result of investigating the effect of inhibiting the activity of acetylcholinesterase (AChE) of a culture of a *Pediococcus inopinatus* LB-400 strain of the present disclosure (FIG. 10a) and EVs derived from the LB-400 strain (FIG. 10b).
Figure 10B:
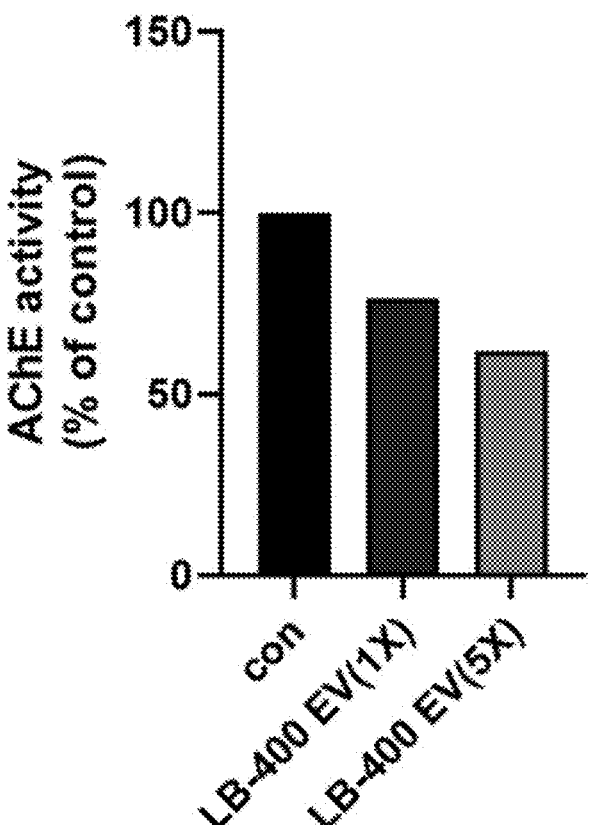

13. Investigation of Effect of Inhibiting the Activity of Acetylcholinesterase (AChE) of Culture of *Pediococcus inopinatus* and EVs In order to investigate the effect of improving memory or cognitive ability of the culture of the *Pediococcus inopinatus* LB-400 strain and extracellular vesicles (EVs) derived therefrom, the effect of inhibiting the activity of acetylcholinesterase (AChE) was evaluated (FIG. 10). The inhibitory effect against acetylcholinesterase (AChE) was measured using an AChE activity assay kit (Sigma). After adding AChE (5 units/mL), each sample (LB-400 culture or EVs) and a buffer solution to a 96-well plate, the reaction mixture was reacted at room temperature for 10 minutes. The enzymatic activity of AChE was determined by measuring absorbance at 410 nm using a microplate reader, with respected to a control group (con) not treated with the sample as 100%. The control group (con) was treated with a medium and PBS of the same volume. The LB-400 culture was used after diluting to 1% or 2%, and the EVs were treated at $4 \times 10^5$ particles/mL ($1 \times$) or $2 \times 10^6$ particles/mL ($5 \times$).

14. Investigation of Effect of Reducing Inflammatory Cytokine Production of EVs Derived from *Pediococcus inopinatus*

Figure 11:
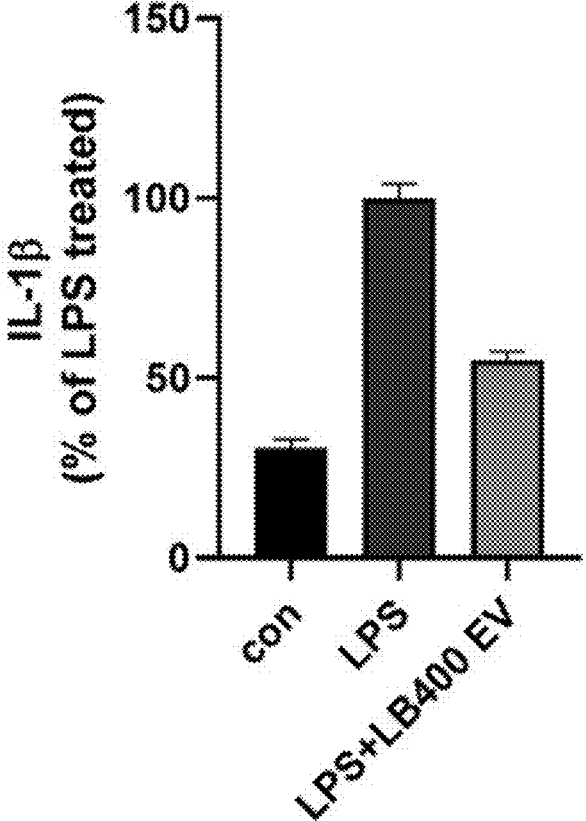
FIG. 11 shows a result of investigating the effect of reducing the production of the inflammatory cytokine IL-1β in microglia (BV2 cells) when EVs derived from a *Pediococcus inopinatus* LB-400 strain of the present disclosure are treated together with LPS.

The effect of reducing the production of the inflammatory cytokine IL-1β of extracellular vesicles (EVs) derived from the *Pediococcus inopinatus* LB-400 strain was investigated (FIG. 11). Experiment was conducted for a cell supernatant obtained by treating cells with LPS and EVs using an IL-1β ELISA kit (Invitrogen). IL-1β production was determined by measuring absorbance at 450 nm using a Multiskan sky microplate spectrophotometer (Thermo Scientific, USA). LPS (lipopolysaccharide) was used after diluting with a medium to 200 ng/mL. The EVs were treated at $1 \times 10^7$ particles/mL, and a control group (con) was treated with PBS of the same volume.

15. Investigation of Effect of Increasing Anti-Inflammatory Cytokine Production of EVs Derived from *Pediococcus inopinatus*

Figure 12:
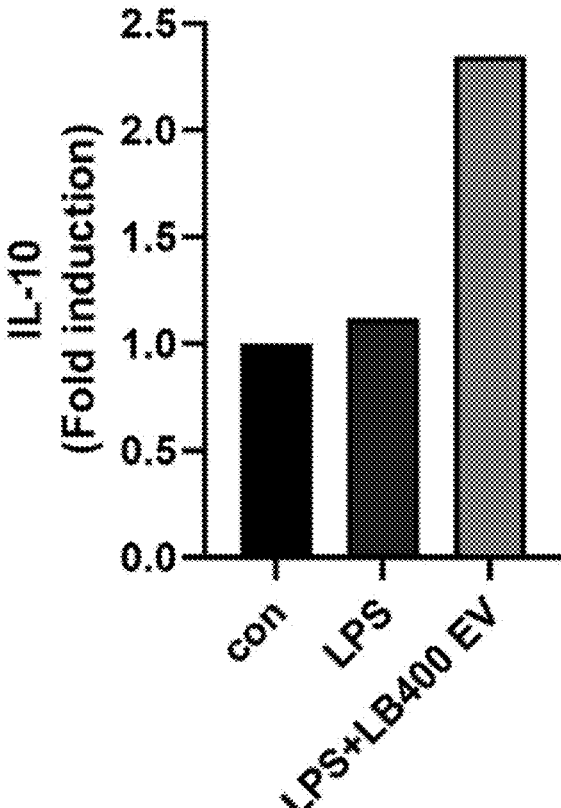
FIG. 12 shows a result of investigating the effect of increasing the production of the anti-inflammatory cytokine IL-10 in microglia (BV2 cells) when EVs derived from a *Pediococcus inopinatus* LB-400 strain of the present disclosure are treated together with LPS.

The effect of increasing the production of the anti-inflammatory cytokine IL-10 of extracellular vesicles (EVs) derived from the *Pediococcus inopinatus* LB-400 strain was investigated (FIG. 12). Experiment was conducted for a cell supernatant obtained by treating cells with LPS and EVs using an IL-10 ELISA kit (MyBioSource). IL-10 production was determined by measuring absorbance at 450 nm using a Multiskan sky microplate spectrophotometer (Thermo Scientific, USA). LPS (lipopolysaccharide) was used after diluting with a medium to 200 ng/mL. The EVs were treated at $1 \times 10^7$ particles/mL, and a control group (con) was treated with PBS of the same volume.

Although the present disclosure was described using the examples, those having ordinary knowledge in the art will be able to change and modify the present disclosure without departing from the technical idea of the present disclosure and such changes or modifications are also included in the scope of the present disclosure.

*Pediococcus inopinatus* WIKIM27

Depository agency: Korean Culture Center of Microorganisms

Yurim B/D 45, Hongjenae-2ga-gil Seodaemun-gu, SEOUL 03641, Republic of Korea

Accession number: KCCM12653P

Date of deposition: Jan. 14, 2020

The invention claimed is:

1. A method for alleviating a brain disease in a subject in need thereof, comprising administering a therapeutically effective amount of extracellular vesicles derived from the *Pediococcus inopinatus* or a culture thereof, to the subject, wherein the brain disease is one or more disease selected from the group consisting of Parkinson's disease, Alzheimer's disease, Huntington's disease, Lou Gehrig's disease (amyotrophic lateral sclerosis), stroke, multiple sclerosis, learning disorder, cognitive impairment, neuroinflammation, neuronal damage, and memory impairment.

2. The method according to claim 1, wherein the *Pediococcus inopinatus* is *Pediococcus inopinatus* WIKIM27 (accession number KCCM12653P).

3. The method according to claim 1, wherein the brain disease is neuroinflammation.

4. The method according to claim 1, wherein the brain disease is neuronal damage.

5. The method according to claim 1, wherein the brain disease is memory impairment.

6. The method according to claim 1, wherein the brain disease is learning disorder, cognitive impairment or Alzheimer's disease.

7. A method for preparing a composition for alleviating a brain disease, comprising:

(a) preparing a *Pediococcus inopinatus* strain;

(b) culturing the strain in a culture medium; and (c) separating extracellular vesicles from the strain or the culture medium, wherein the brain disease is one or more disease selected from the group consisting of Parkinson's disease, Alzheimer's disease, Huntington's disease, Lou Gehrig's disease (amyotrophic lateral sclerosis), stroke, multiple sclerosis, learning disorder, cognitive impairment, neuroinflammation, neuronal damage, and memory impairment.

8. A method for preparing a composition for alleviating a brain disease, comprising preparing extracellular vesicles derived from *Pediococcus inopinatus* or a culture thereof, wherein the brain disease is one or more disease selected from the group consisting of Parkinson's disease, Alzheimer's disease, Huntington's disease, Lou Gehrig's disease (amyotrophic lateral sclerosis), stroke, multiple sclerosis, learning disorder, cognitive impairment, neuroinflammation, neuronal damage, and memory impairment.

* * * * *